US009771611B2

(12) United States Patent
Hauke (10) Patent No.: US 9,771,611 B2
(45) Date of Patent: Sep. 26, 2017

(54) METHOD FOR DETECTING A CHROMOSOMAL ABERRATION (75) Inventor: Sven Hauke, Bremen (DE)

(73) Assignee: Zytovision GmbH (DE)

( * ) Notice: Subject to any disclaimer, the term of this patent is extended or adjusted under 35 U.S.C. 154(b) by 22 days.

(21) Appl. No.: 14/115,275

(22) PCT Filed: Apr. 27, 2012

(86) PCT No.: PCT/EP2012/001825
§ 371 (c)(1),
(2), (4) Date: Nov. 1, 2013

(87) PCT Pub. No.: WO2012/150022
PCT Pub. Date: Nov. 8, 2012

(65) Prior Publication Data
US 2014/0065618 A1  Mar. 6, 2014

(30) Foreign Application Priority Data
May 2, 2011 (DE) .................. 10 2011 100 242

(51) Int. Cl.
C07H 21/04 (2006.01)
C12Q 1/68 (2006.01)

(52) U.S. Cl.
CPC ......... C12Q 1/6818 (2013.01); C12Q 1/6841 (2013.01); C12Q 1/6886 (2013.01); C12Q 2600/156 (2013.01)

(58) Field of Classification Search
None
See application file for complete search history.

(56) References Cited

U.S. PATENT DOCUMENTS 7,306,916 B2 * 12/2007 Poulsen .................. B82Y 5/00
435/6.16
7,964,345 B2 * 6/2011 Palanisamy .......... C12Q 1/6841
435/6.11

(Continued)

FOREIGN PATENT DOCUMENTS

EP  0549709 B1  1/1997
EP  1035215 B1  7/2006

(Continued)

OTHER PUBLICATIONS

Ryan Bishop (Bioscience Horizons, vol. 3, No. 1, Mar. 2010, pp. 85-95).*

(Continued)

Primary Examiner — Jeanine A Goldberg
(74) Attorney, Agent, or Firm — Cohen & Grigsby, P.C.

(57) ABSTRACT

The invention relates to a method for detecting several different chromosomes or DNA regions in a cell in order to provide evidence for structural chromosomal aberrations, wherein the chromosomal aberrations have at least two breaking point regions within a chromosome, on the basis of directly or indirectly labeled nucleic acid fragments (probes), wherein: a first probe labeled with label A (probe A) and a second probe labeled with label B (probe B) flank a breaking point region 1, and form the fusion signals A-B; and two probes, a third and a fourth, each labeled with a label C (probes C), flank a breaking point region 2, and form the fusion signals C-C, wherein the above-mentioned fusion signals change in the event of a chromosomal aberration to fusion signals A-C and to fusion signals B-C.

16 Claims, 4 Drawing Sheets

(56) References Cited

U.S. PATENT DOCUMENTS

| | | | |
|---|---|---|---|
| 2012/0237930 A1* | 9/2012 | Nitta | C12Q 1/6841 435/6.11 |
| 2013/0102006 A1* | 4/2013 | Takeuchi | G01N 33/57484 435/6.12 |

FOREIGN PATENT DOCUMENTS

| | | |
|---|---|---|
| WO | 9205185 A1 | 4/1992 |
| WO | 02093130 A2 | 11/2002 |
| WO | 2005111235 A2 | 11/2005 |
| WO | 2007028031 A2 | 3/2007 |
| WO | 2009102446 A2 | 8/2009 |

OTHER PUBLICATIONS

Invitrogen (Molecular Probes Handbook, A guide to fluorescent probes and labeling technologies, 11th Edition, 2010, Chapter 8).*

Lowenstein et al. (Mol Biol of the Cell, vol. 15, pp. 5678-5692, Dec. 2004).*

Boomer T et al: "Detection of E2A translocations in leukemias via fluorescence in situ hybridization.", Leukemia : Official Journal of the Leukemia Society of America, Leukemia Research Fund, U.K Jan. 2001 LNKD-PUBMED:11243406, vol. 15, No. 1, Jan. 2001 (Jan. 1, 2001), pp. 95-102, XP002680766, ISSN: 0887-6924.

Burg Van Der M et al: "Split-signal FISH for detection of chromosome aberrations in acute lymphoblastic leukemia", Leukemia, MacMillan Press Ltd, US, vol. 18, No. 5, May 1, 2004 (May 1, 2004), pp. 895-908, XP002359905, ISSN: 0887-6924, DOI: 10.1038/SJ.LEU.2403340.

Hopman A H et al: "Multi-colour brightfield in situ hybridisation on tissue sections.", Histochemistry and Cell Biology Oct.-Nov. 1997 LNKD-PUBMED:9387920, vol. 108, No. 4-5, Oct. 1997 (Oct. 1, 1997), pp. 291-298, XP002680765, ISSN: 0948-6143.

Osoegawa Atsushi et al: "Incidentally proven pulmonary "ALKoma".", Internal Medicine (Tokyo, Japan) 2010 LNKD-PUBMED:20228600, vol. 49, No. 6, 2010, pp. 603-606, XP002680793, ISSN: 1349-7235.

Van Der Burg, et al., "Rapid and sensitive detection of all types of MLL gene translocations with a single FISH probe set", Leukemia (1999) vol. 13, pp. 2107-2113.

Laasko, et al., "Dual-color chromogenic in situ hybridization for testing of HER-2 oncogene amplification in archival breast tumours", Journal of Pathology (2006) vol. 210, pp. 3-9.

Wan, et al., "Derivitive chromosome 9 deletions in chronic myeloid leukamia: interpretation of atypical D-FISH pattern", J Clin Pathol (2003), vol. 56, pp. 471-474.

Tanner, et al., "Chromogenic in situ hybridization", American Journal of Pathology (2000), vol. 157, pp. 1467-1472.

Fink et al., "Validation of a new three-color fluorescence in situ hybridization (FISH) method to detect CHIC2 deletion, FIP1L1/PDGFRA fusion and PDGFRA translocation", Leukemia Research (2009), vol. 33, pp. 843-846.

Dewald, et al., "Highly Sensitive Fluorescence in Situ Hybridization Method to Detect Double BCR/ABL Fusion and Monitor Response to Therapy in Chronic Myeloid Leukemia", Blood (1998), vol. 92, No. 9., pp. 3357-3365.

Carbone, et al., "Delineation of HER2 Gene Status in Breast Carcinoma by Silver in Situ Hybridization is Reproducible among Laboratories and Pathologists", Journal of Molecular Diagnostics, (2008), vol. 10, No. 6, pp. 527-536.

Mayr et al., "Chromogenic in situ hybridization for Her-2/neu-oncogene in breast cancer: comparison of a new dual-colour chromogenic in situ hybridization with immunohistochemistry and fluorescence in situ hybridization", Histopathology, (2009), vol. 55, pp. 716-723.

Dewald et al., "A Multicenter Investigation with D-FISH BCR/ABL1 Probes", Cancer Genet Cytogenet, (2000), vol. 116, pp. 97-104.

* cited by examiner

METHOD FOR DETECTING A CHROMOSOMAL ABERRATION

CROSS-REFERENCE TO RELATED APPLICATIONS

The present application is a national stage application under 35 USC 371 of International Application No. PCT/EP2012/001825 which claims the benefit of German Patent Application No. 10 2011 100242.5 filed on May 2, 2011, which is incorporated herein by reference in its entirety.

BACKGROUND

1. Technical Field of the Invention

The present invention relates to a method for detecting multiple different chromosome regions or DNA regions in a cell for detection of structural chromosome aberrations, wherein the chromosome aberrations have at least two breaking point regions within a chromosome, based on directly or indirectly labeled nucleic acid fragments (probes) and a preparation suitable for this method.

2. Description of the Related Art

Many malignancies are based on structural chromosome mutations, such as translocations, inversions and segmental duplications. These changes are usually detected as predictive, prognostic or differential diagnostic markers by in situ hybridization (ISH) using fluorescence-labeled (fluorescence ISH (FISH)) nucleic acid fragments, so-called probes or hapten-labeled probes, which are then detected with antibodies and visualized by color reactions under light microscopy (bright field ISH (BrISH)—also including chromogenic ISH (CISH) and silver-enhanced ISH (SISH)).

The advantage of FISH here is that multiple genomic regions can be detected simultaneously but still differentiated clearly from one another without increased effort in performing the method. To do so, nucleic acid fragments, which address different genomic regions, are labeled with, i.e., coupled to, different fluorescent dyes, which differ from one another in their absorption spectrum and/or emissions spectrum. When such multicolor probes are used, e.g., on metaphase chromosome preparations or on interphase cell nucleus preparations, the individual colors can be represented separately from one another by using specific microscope filter sets, which conduct precisely defined wavelength ranges of light for excitation of dyes onto the preparation and allow precisely defined wavelength ranges of light emitted by the dyes to pass through to the analyzer (so-called single-bandpass filter set), or the different fluorescent signals of multiple fragments are represented at the same time (in the case of two different fluorescent dyes, we speak here of a dual-bandpass filter set).

However, there are definite limits to simultaneous visualization because the absorption ranges and emission ranges of the dyes are often so close to one another that they cannot be separated from one another by the microscope filter sets. Furthermore, two superimposed signals of different colors result in the perception of mixed colors (e.g., yielding red (or orange) and green and thereby yellow), which cannot be differentiated from signals of the same color, which are the result of another fluorochrome and are not formed by overlapping. For these reasons, usually only two colors (orange/red and green) or three colors (orange/red and green simultaneously with a blue nuclear counterstain (DAPI)) are observed simultaneously in routine FISH. Approximately the same restrictions as those that can be visualized for FISH also apply to BrISH, where the state of the art is to use two haptens, usually selected from the group of biotin, dinitrophenyl (DNP) and digoxigenin, and two antibody-coupled enzymes, usually alkaline phosphatase and peroxidase (Carbone et al., 2008; Hopman et al., 1997; Laakso et al., 2006; Mayr et al., 2009; Tanner et al., 2000).

These restrictions in simultaneous visualization have a definitive influence on the compositions of the probes for detection of translocations and inversions. There are in principle two definitive techniques and fundamental probe compositions here: the principle of the formation of fusion signals (so-called dual-color-dual-fusion approaches) (WO 02093130, Dewald et al., 1998; Dewald et al., 2000; Wan et al., 2003) and/or of the separation of fusion signals (so-called dual-color-break-apart or dual-color-split approaches) (van der Burg et al., 1999; Boomer et al., 2001; van der Burg et al., 2004). In the following discussion of these two principles and derived signal patterns, it should be noted that a normal cell is usually diploid, i.e., each allele is present twice. Since usually only one of the two alleles is affected by aberrations, then the normal signal of the allele not affected by the aberration will usually be visible in addition to the aberrant signal. For a better understanding, the signal pattern of the normal signal is not always described explicitly below.

In dual-color-dual-fusion approaches, the region of breaking point 1 is flanked proximally and distally by nucleic acid fragments of the same color (e.g., orange), while the region of the breaking point 2, i.e., the reciprocal translocation partner, is flanked proximally and distally by nucleic acid fragments of a second color (e.g., green). The normal situation, i.e., without chromosomal breaks in the region of the two translocation partners is characterized here by a green signal and by a spatially separate orange signal.

In the case of a reciprocal translation, there are breaks within the breaking points of the two translocation partners, and the proximal region of the one translocation partner is fused to the distal region of the other partner and vice-versa. This therefore results in two green/orange signal pairs, also known as fusion signals, because the different colored signals often overlap, so a mixed color signal is visible. The disadvantage of these probe techniques is that the fusion signals are formed only when the breaking points of the two translocation partners are situated in the region of the respective labeled nucleic acid fragments. In translocations affecting only one of the two partners, no fusion signals are formed. This results only in the creation of an additional signal having the color of the signal which is characteristic of the partner affected by the translocation. In other words, an additional green signal, for example, is formed when the breaking point of the translocation is in the region covered by the nucleic acids labeled with green fluorochrome. However, such additional signals may often be covered by other cell nuclei, which may be situated close to one of the other signals of the same color and thus cannot be perceived as an additional signal or are lost due to tissue section artifacts. In this case, there may be a misdiagnosis because a translocation affecting only the one translocation partner is not perceived.

In dual-color-dual-fusion approaches, the region of breaking point 1 is flanked proximally and distally by nucleic acid fragments of the same color (e.g., orange), while the region of the breaking point 2, i.e., the reciprocal translocation partner, is flanked proximally and distally by nucleic acid fragments of a second color (e.g., green). The normal situation, i.e., without chromosomal breaks in the region of the two translocation partners, is characterized here by a green signal and by a spatially separate orange signal.

The disadvantage of these probe compositions is that it is impossible to obtain information about the translocation partner involved. Furthermore, due to the sighting axis with which the observer views the interphase cell nucleus, for example, it may happen that two spatially separate signals, which are situated one above the other with respect to the viewing axis, are still perceived as fusion signals.

In addition to the two-color applications mentioned above, three-color, four-color and five-color probes are also used in FISH analyses. In addition to the much stronger standard fluorescent colors orange, red and green, the other weaker colors that are available, e.g., gold or red or blue, are also used. Therefore, in routine applications, for example, multicolor FISH probes are used only for detection of deletions or amplifications (EP 1035215 B1, WO 2007/028031, EP 0549709 B1) because repetitive sequences can usually be accessed here in the labelings for amplification of the color intensities, e.g., blue and gold.

The triple FISH approaches described by Finkel et al. (2009) address the detection of different translocation events, which may cluster side-by-side in a chromosomal region (i.e., different genes located in proximity are affected). For the corresponding analysis of the signal patterns, only two colors which detect a single aberration are used, wherein the third color then does not play a role.

With respect to BrISH using more than two colors, Hopman et al. (1997) describe how a chromogenic triple in situ hybridization is performed, aimed in general at detecting three repetitive chromosomal regions. According to the state of the art today, translocations are detected by means of BrISH only using two haptens and thus two colors.

Also unknown is the use of the BrISH method for detection of inversions and insertions.

Inversions and in particular small inversions cannot be detected with the techniques and methods described in the patent applications WO 02093130 A3 and WO 2005/111235 A2. WO 2005/111235 A2 describes a method involving the use of three color probes. However, the chromosomal region labeled by the third label of a probe is not affected directly by a change so that in a change in chromosome structure, the first fusion signal is eliminated, resulting in a new split signal and a new fusion signal. It is difficult or impossible to distinguish this event from a normal situation in the case of inversions, in particular small inversions.

WO 02093130 A3 discloses a method for detection of chromosomal translocations using two or four labels/dyes, wherein the probes are hybridized for different chromosomes. This method is suitable for detection of inversions only to a limited extent. Furthermore the analytical method is much more complex due to the plurality of signals that can be derived from four labels/dyes.

All the methods and probes compositions currently available for BrISH and FISH in conjunction with inversions, in particular but not limited to tumors, have shortcomings. There are no probe compositions and methods and their resulting signal patterns which allow reliable detection of an inversion in all cases. This aberration event is not usually detected in the case of small inversions in particular, i.e., inversions of short genomic segments (for example, regions of less than 20 Mb).

The object of the present invention is therefore to provide a method with which reliable detection of structural chromosome aberrations is made possible, wherein the chromosome aberrations have at least two breaking point regions within a chromosome.

SUMMARY

The presently disclosed invention overcomes many of the shortcomings of the prior art by providing a method for the detection of multiple different chromosome or DNA regions in a cell for the identification of structural chromosome aberrations, wherein a first probe (probe A), labeled with a label A, and a second probe (probe B), labeled with a label B, flank a breaking point region 1, forming fusion signals A-B, and two probes, the third and fourth probes, each labeled with a label C (probes C), flank a breaking point region 2, forming fusion signals C-C, wherein the fusion signals mentioned above change to fusion signals A-C and fusion signals B-C in the event of a chromosome aberration.

Probes are understood to be nucleic acid fragments marked with a certain label. The labeled nucleic acid fragments (probes) are preferably polynucleotides, modified polynucleotides or modified nucleic acid fragments or oligonucleotides or modified oligonucleotides.

The nucleic acid fragments may have different labels A, B and C, so different probes A, B and C are also formed. A combination of three different fluorescent dyes is therefore used in FISH or three different reporter molecules are used in BrISH for labeling of the nucleic acid fragments (or polynucleotides in general or also oligonucleotides).

The label may be selected from the group of dyes, dye substrates, chemiluminescent dyes (e.g., acridinium), radio-isotopes, spin labels, enzymes (e.g., alkaline phosphatase, horseradish peroxidase, soybean peroxidase and/or beta-galactosidase), haptens (e.g., dioxigenin, biotin, 5(6)-carboxyfluorescein, rhodamine, bromodeoxyuridine, acetylaminofluorene, trinitrophenol, trinitrophenol derivative, estradiol and/or DNP), quantum dots, beads, aminohexyls, pyrenes and fluorescent dyes (e.g., fluorescein, fluorescein derivative, 5(6)-carboxyfluorescein, coumarin, coumarin derivative, rhodamine, rhodamine derivative, tetramethylrhodamine, lissamine, Texas red, AMCA, TRITC, IR dye, Alexa dye, Dyomics dye, phycoerythrine, Cascade blue, Oregon green 488, Pacific blue and/or Rhodamine green).

The method according to the presently disclosed invention may be performed by means of the FISH method using three directly incorporated fluorescent dyes for the emission ranges green, orange/red and blue. This method can also be performed by means of the FISH method using three directly incorporated fluorescent dyes for the emission ranges green, red and gold.

The method according to the presently disclosed invention may be performed by means of the BrISH method using biotin, digoxigenin and DNP bind to antibody-coupled alkaline phosphatase, antibody-coupled peroxidase and antibody-coupled beta-galactosidase.

The method according to the presently disclosed invention is for the detection of inversions, insertion and/or duplication. Alternately, the method according to the presently disclosed invention is for detection of inversions, insertions and/or duplications of short genomic sections.

In various embodiments of the method, inverted, inserted and/or duplicated genomic sections in the range of less than 20 Mb, preferably less than 15 Mb, especially preferably less than 10 Mb, and even more preferably less than 5 Mb are detected.

In embodiments, the altered fusion signals A-C or B-C are visible in the signal pattern as fusion signal A-C and signal C/signal B or as fusion signal B-C and signal C/signal A in a large breaking point region.

Various embodiments of the method provide for detection of differentiation inversions and translocations. Further, embodiments of the method provide for detection of inversions, wherein the inversion inv(2)(p22-p21p23) and/or the genes ALK and/or EML4 are affected.

The method according to the presently disclosed invention is preferably used for detection of inversions, wherein the inversion inv(2)(p22-p21p23) and/or the ALK and/or EML4 genes are affected.

Another subject matter of the presently disclosed invention is a preparation for detection of multiple different chromosome or DNA regions in a cell for detection of structural chromosome aberrations, wherein the chromosome aberrations have at least two breaking point regions on a chromosome based on directly or indirectly labeled nucleic acid fragments (probes), comprising a first probe (probe A), labeled with a label A, and a second probe (probe B), labeled with a label B, flank a breaking point region 1, forming fusion signals A-B, and two probes, the third and fourth probes, each labeled with a label C (probes C), flank a breaking point region 2, forming fusion signals C-C, wherein the fusion signals mentioned above change to fusion signals A-C and fusion signals B-C in the event of a chromosome aberration.

The preparation according to the invention preferably has probes which are labeled with the labels mentioned above.

BRIEF DESCRIPTION OF THE DRAWINGS

Aspects, features, benefits and advantages of the embodiments herein will be apparent with regard to the following description, appended claims, and accompanying drawings, which show:

DETAILED DESCRIPTION

The presently disclosed invention relates to a method for the detection of multiple different chromosome or DNA regions in a cell for the identification of structural chromosome aberrations. In this method, a first probe (probe A), labeled with a label A, and a second probe (probe B), labeled with a label B, flank a breaking point region 1, forming fusion signals A-B, and two probes, the third and fourth probes, each labeled with a label C (probes C), flank a breaking point region 2, forming fusion signals C-C, wherein the fusion signals mentioned above change to fusion signals A-C and fusion signals B-C in the event of a chromosome aberration.

Breaking point region 1 and breaking point region 2 describe possible breaking points within a chromosome.

The term "flank" is understood here to mean that probe A and probe B each hybridize on one side of the breaking point region 1 and similarly probes C each hybridize on one side of the breaking point region 2.

It is also conceivable that a single probe C may span the breaking point region 2 in order to obtain the same effect, namely the formation of fusion signals C-C.

Probes are understood to be nucleic acid fragments marked with a certain label.

The method according to the invention allows, for the first time, a clear-cut detection of multiple different chromosome or DNA regions in a cell for the identification of structural chromosome aberrations in comparison with the aforementioned methods and compositions. Further, the method makes it possible to detect inversions for the first time ever, in particular smaller genomic inversions, as well as to positively differentiate them from translocations.

The labeled nucleic acid fragments (probes) are preferably polynucleotides, modified polynucleotides or modified nucleic acid fragments or oligonucleotides or modified oligonucleotides.

For example, those skilled in the art are familiar with PNA and LNA for modified polynucleotides.

The nucleic acid fragments preferably have different labels A, B and C, so different probes A, B and C are also formed.

A combination of three different fluorescent dyes is therefore used in FISH or three different reporter molecules are used in BrISH for labeling of the nucleic acid fragments (or polynucleotides in general or also oligonucleotides).

The label is preferably selected from the group of dyes, dye substrates, chemiluminescent dyes (e.g., acridinium), radioisotopes, spin labels, enzymes (e.g., alkaline phosphatase, horseradish peroxidase, soybean peroxidase and/or beta-galactosidase), haptens (e.g., dioxigenin, biotin, 5(6)-carboxyfluorescein, rhodamine, bromodeoxyuridine, acetylaminofluorene, trinitrophenol, trinitrophenol derivative, estradiol and/or DNP), quantum dots, beads, aminohexyls, pyrenes and fluorescent dyes (e.g., fluorescein, fluorescein derivative, 5(6)-carboxyfluorescein, coumarin, coumarin derivative, rhodamine, rhodamine derivative, tetramethyirhodamine, lissamine, Texas red, AMCA, TRITC, IR dye, Alexa dye, Dyomics dye, phycoerythrine, Cascade blue, Oregon green 488, Pacific blue and/or Rhodamine green).

The method according to the invention may preferably be performed by means of the FISH method using three directly incorporated fluorescent dyes for the emission ranges green, orange/red and blue.

This method can also be performed by means of the FISH method using three directly incorporated fluorescent dyes for the emission ranges green, red and gold.

The analysis is preferably performed by analysis of fluorescent signals.

The method according to the invention is preferably performed by means of the BrISH method using biotin, digoxigenin and DNP bind to antibody-coupled alkaline phosphatase, antibody-coupled peroxidase and antibody-coupled beta-galactosidase.

It has surprisingly been found that in the method according to the invention, new fusion signals A-C and B-C are formed, wherein the fusion signals A-C and/or B-C are formed by a two-color split event of the fusion signals A-B and by a single-color split event of the fusion signals C-C. Two new fusion signals may be considered here as the resulting signal pattern (with simultaneous use/observation/analysis of the third color/third label). The method according to the invention thus surprisingly allows for the first time the aforementioned detection of the aforementioned aberrations which are impossible or are possible only to a very inadequate extent with the prior art. Simultaneous analysis of the third color/third label in addition to the two other colors/labels permits identification of the aberration for the first time or unambiguously.

In the case of genomic inversions as well, in particular but not limited to smaller inversions with genomic sections affected by the inversion, of less than 20 Mb, the spatial separation of the signals may turn out to be so minor that they are still perceived as a fusion signal. In these cases, this may result in a misdiagnosis because a translocation is not perceived as such.

The method according to the invention is preferably suitable for detection of inversions and/or insertion and/or duplication.

The method according to the invention is preferably for detection of inversions, insertions and/or duplication of short genomic sections.

The inverted, inserted and/or duplicated genomic sections are preferably in the range of less than 20 Mb, preferably less than 15 Mb, especially preferably less than 10 Mb and even more preferably less than 5 Mb.

For inversions of short genomic sections, two newly assembled fusion signals are formed and are clearly discernible by means of the conventional suitable filter sets, for example, in a FISH analysis in the interphase. However, the possibility cannot be ruled out that in the case of larger breaking point regions, the fusion signals A-C or B-C may be separated spatially, so that the signals are no longer clearly discernible as fusion signals. At least in these cases, there is then a signal C separately.

It is also possible to differentiate inversions from translocations with the help of the method according to the invention.

The method according to the invention is preferably used for detection of inversions, wherein the inversion inv(2) (p22-p21p23) and/or the ALK and/or EML4 genes are affected.

Fundamentally, at least two of the fluorescent colors may be perceptible simultaneously in FISH through a suitable filter set, which allows a quick and simple screening similar to the two-color probe approaches mentioned above, but this also offers additional diagnostic certainty.

The advantages of genomic inversion detection by means of the novel probe compositions and the novel ISH techniques are described in greater detail below:

Reliable or unambiguous detection of the inversion of short genomic sections (regions smaller than 20 Mb) is impossible using traditional probe compositions. Furthermore, detection of the inversion of larger genomic sections (regions larger than 20 Mb), is often possible only with great difficulty. There are various state-of-the-art probe concepts here. In the simplest case, only one of the two breaking point regions is considered using a dual-color-break-apart approach. In the case of an inversion, there is a spatial separation of the fluorescence signals. However, this signal separation also occurs with traditional reciprocal translocations involving the breaking point region, from which a differentiation is impossible using this probe concept.

Another disadvantage is that a signal separation of the fusion signal into close but separately perceptible fluorescence signals often also occurs with dual-color-break-apart probes and techniques in the non-rearranged state. If the genomic section of the inversion per se is only very short (e.g., less than 20 Mb), this can lead to the expected spatial signal separation being only insignificantly greater, so it may be overlooked. It is thus impossible to differentiate between inversion and reciprocal translocation with this approach. Furthermore, aberrant situations can also be misinterpreted as being non-rearranged.

In the ease of a dual-color-dual-fusion approach, the proximal breaking point region would be spanned by nucleic acid fragments labeled with green, for example, and the distal breaking point region would be spanned by nucleic acid fragments labeled with orange, for example. In the case of the inversion of a short genomic section of less than 20 Mb, for example, there would be two green signals very close together and there would also be two orange signals very close together. Thus, in signal super-positioning, two fusion signals very close together would be formed but often could not be reliably perceived as two separate fusion signals, for example, even with a corresponding dual-bandpass filter set. A remedy to this situation could be created, for example, by using single-bandpass filter sets specifically for the two signal colors. However, this would complicate the analysis process and make it slower. In addition, elongated signals, like a string of pearls, are often formed in sections of de-condensed chromatin, even with normal alleles, such that two of these signals, which are separated spatially because of an inversion, cannot necessarily be differentiated. Misinterpreting two fusion signals close together as being just one fusion signal would result in a false-negative diagnostic result.

The probe composition of the present invention also combines the dual-color-break-apart approach for the detection of the break in one of the two breaking point regions with a single-color-break-apart approach using a third label, e.g., fluorochrome in FISH, e.g., blue, which can be detected separately from the first two labels, e.g., dyes (e.g., green and orange) for detection of the break in the second breaking point region. In the case of an inversion, there is usually a perceptible separation of the fusion signals, which is usually perceptible in a FISH application in a dual-bandpass filter set, for example, into a spatially separate green signal and orange signal. At the same time, for example, perceptible in a second filter set specifically for blue, the blue signal is separated into two spatially separate signals due to the break in the second breaking point region. In contrast with the traditional approaches, an inversion is thus characterized by two events that are perceptible separately from one another, which leads to a diagnostic result that is definitely more reliable, in particular in the case of unclear signal patterns. Thus, in the case of an unclear green-orange signal separation, there may be confirmation by analysis in the single-bandpass filter set for the blue signal. If there is an additional blue signal here, and if a blue signal is co-localized with a green signal and an orange signal, this is considered to be confirmation of the inversion. However, if there is a normal blue signal pattern, then the green-orange signal in question is also considered to be non-aberrant. In the case of an unambiguous signal separation into a green signal and an orange signal, the analysis of the blue signal pattern serves to differentiate between an inversion (in this case, there is an additional blue signal) and a translocation with an unknown translocation partner (in this case, there is a normal blue signal pattern).

Another subject matter of the present invention is a preparation according to the invention for detection of multiple different chromosome regions or DNA regions in a cell for detection of structural chromosome aberrations, wherein the chromosome aberrations have at least two breaking point regions on a chromosome based on directly or indirectly labeled nucleic acid fragments (probes), comprising a first probe (probe A), labeled with a label A, and a second probe (probe B), labeled with a label B, flank a breaking point region 1, forming fusion signals A-B, and two probes, the third and fourth probes, each labeled with a label C (probes C), flank a breaking point region 2, forming fusion signals C-C, wherein the fusion signals mentioned above change to fusion signals A-C and fusion signals B-C in the event of a chromosome aberration.

Figure 1:
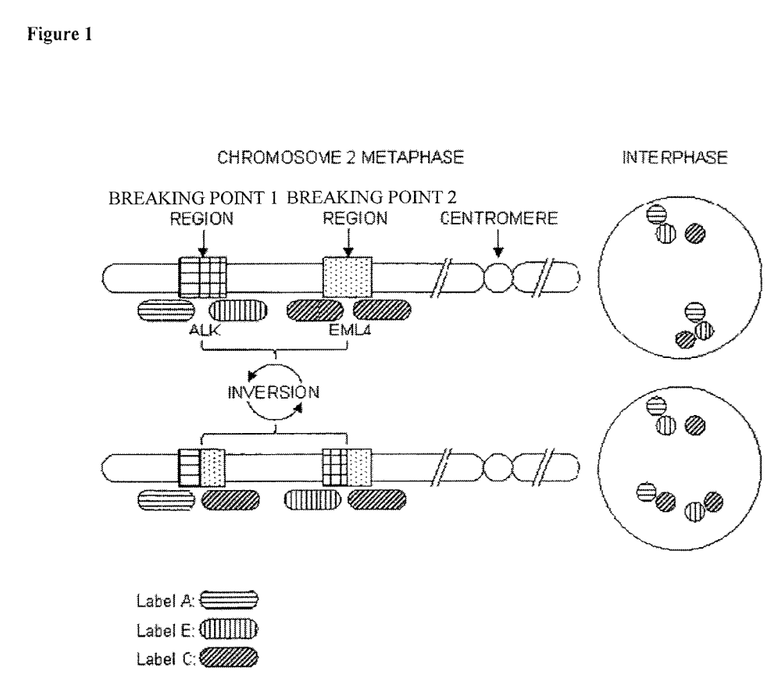
FIG. 1 illustrates a schematic diagram of a method according to the present invention for detection of an inversion.

Referring now to the drawings, FIG. 1 shows a schematic diagram of a method according to the invention for detection of an inversion using three labels. This shows the signal pattern in the inversion inv(2)(p22-p21p23), which relates to the ALK and EML4 genes. Labels A and B of a triple ISH probe each flank one side of the breaking point region 1 (ALK) and label C flanks one side of the breaking point region 2 (EML4).

In the interphase of a normal cell (without aberrations, top part of the figure), two fusion signals consisting of label A and label B and two signals of label C are discernible. In an interphase affected by an inversion (bottom part of the figure), a new fusion signal A-C occurs, consisting of label A and label C plus a new fusion signal B-C consisting of label B and label C. In addition, there are fusion signals and individual signals of the normal chromosome.

Figure 2:
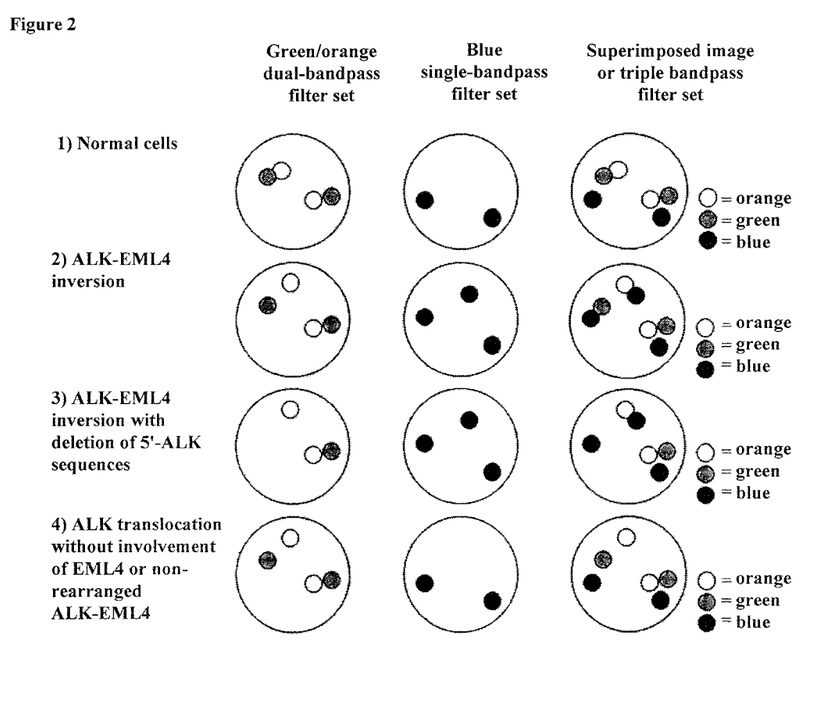
FIG. 2 illustrates a scheme for signal patterns obtained when using a triple FISH probe "ZytoLight SPEC ALK/EML4 TriCheck™ Probe" from the company ZytoVision GmbH.

FIG. 2 shows a scheme for signal patterns when using a triple FISH probe "ZytoLight SPEC ALK/EML4 TriCheck™ Probe" from the company Zytovision. The probe consists of green-labeled polynucleotides (absorption at 503 nm and emission at 528 nm), which are directed in 2p23 against sequences situated proximally to the ALK breaking point region, orange-labeled polynucleotides (absorption at 547 nm and emission at 572 nm), which are directed in 2p23 against sequences situated distally to the ALK breaking point region, as well as blue-labeled polynucleotides (absorption at 426 nm and emission at 480 nm), which are directed in the region 2p21 [against] sequences situated distally and proximally to the EML4 breaking point region.

When using suitable filter sets, the hybridization signals for the ALK gene (2p23) appear as green and orange fluorescent signals, while the hybridization signals for the EML4 gene (2p21) appear as blue fluorescent signals.

In normal cells and/or cells without ALK-EML4 rearrangements, two green/orange fusion signals appear in the interphase when using a suitable dual-bandpass filter set, and two blue signals appear when using a suitable single-bandpass filter set (see FIG. 1).

A 2p21-23 locus affected by an ALK-EML4 inversion is characterized by a separate green signal and a separate orange signal as well as an additional blue signal. The separate green signal and orange signal are each next to a blue signal (see FIG. 2).

A 2p21-23 locus which has a deletion of 5'-ALK sequences and is affected by an ALK-EML4 inversion is characterized by the loss of a green signal and by an additional blue signal. The orange signal here is situated next to a blue signal (see FIG. 3).

A separate green signal and a separate orange signal in combination with a normal number of blue signals (see FIG. 4) stand either for an ALK translocation without including the EML4 or, if the separate green and orange signals are very close to one another, they stand for a non-rearranged 2p21-23 locus.

Figure 3:
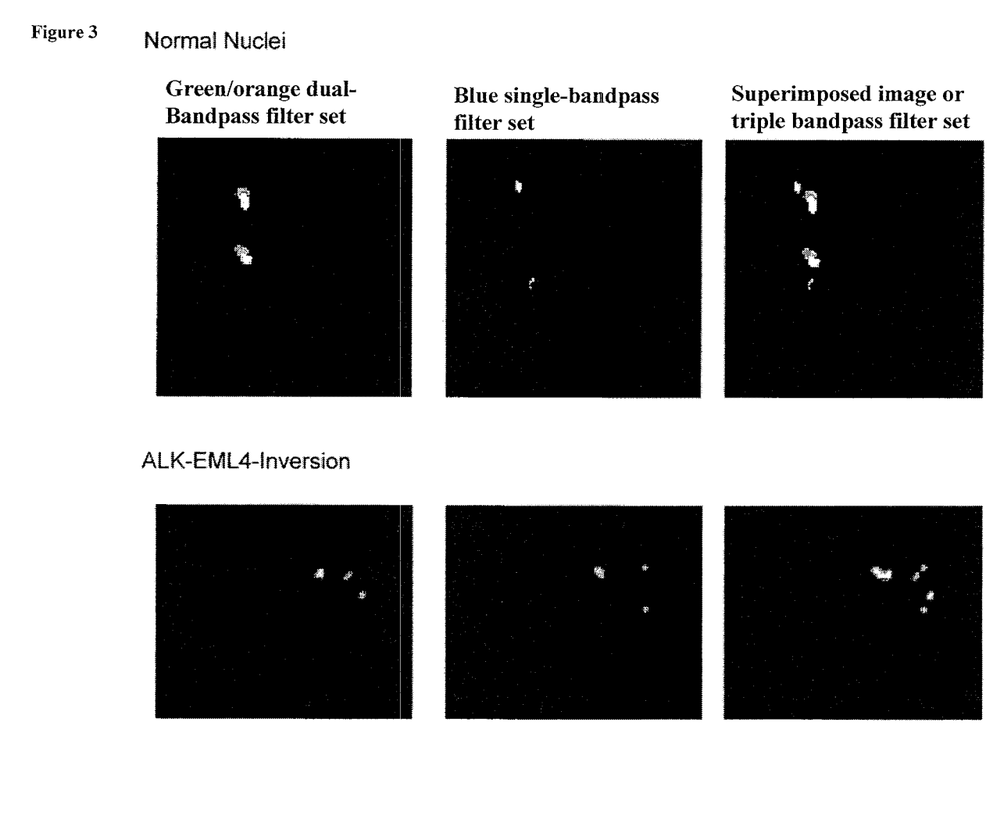
FIG. 3 illustrates FISH analysis for detection of the inversion inv(2)(p22-p21p23) using the triple FISH probe "ZytoLight SPEC ALK/EML4 TriCheck™ Probe"

FIG. 3 shows a FISH analysis for detection of the inversion inv(2)(p22-p21p23) using the triple FISH probe "ZytoLight SPEC ALK/EML4 TriCheck™ Probe." The probe consists of green-labeled polynucleotides (absorption at 503 nm and emission at 528 nm), which are directed in 2p23 against sequences situated proximally to the ALK breaking point region, orange-labeled polynucleotides (absorption at 547 nm and emission ad 572 nm), which are directed in 2p23 against sequences situated distally to the ALK breaking point region as well as blue-labeled polynucleotides (absorption at 426 nm and emission at 480 nm), which are directed in region 2p21 [against] sequences situated distally and proximally to the EML4 breaking point region. This signal pattern can be visualized well using suitable filter sets.

Figure 4:
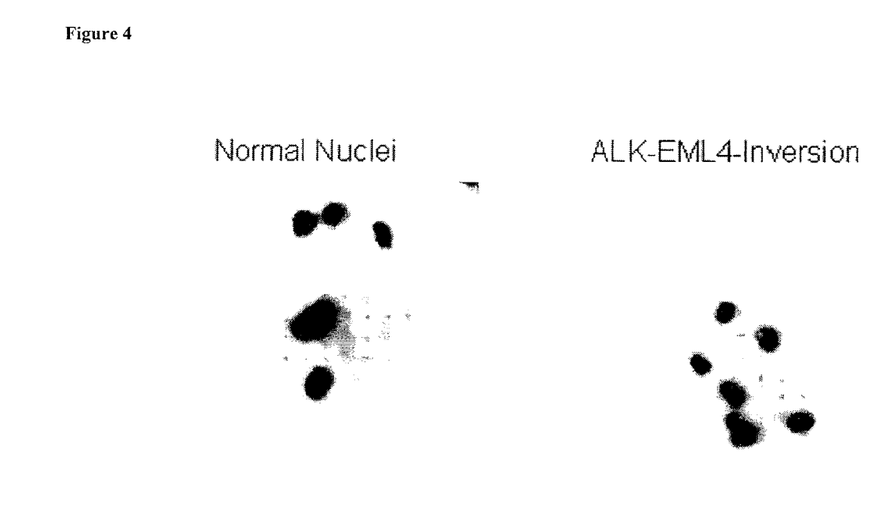
FIG. 4 illustrates CISH analysis for detection of the inversion inv(2)(p22-p21p23) using the triple CISH probe "ZytoDot 2C SPEC ALK/EML4 TriCheck™ Probe" from the company ZytoVision GmbH.

FIG. 4 shows a CISH analysis for detection of the inversion inv(2)(p22-p21p23) using the triple CISH probe "ZytoDot 2C SPEC ALK/EML4 TriCheck™ Probe." This probe consists of digoxigenin-labeled polynucleotides, which are directed in 2p23 against sequences situated proximally to the ALK breaking point region, DNP-labeled polynucleotides which are directed in 2p23 against sequences situated distally to the ALK breaking point region as well as biotin-labeled polynucleotides, which are directed in the 2p21 region [against] sequences situated distally and proximally to the EML4 breaking point region. Detection of the labeling is performed by means of primary (unlabeled) antibodies (anti-DIG/anti-DNP/anti-BIO), which are detected by secondary polymerized enzyme-conjugated antibodies (HRP polymer/AP polymer/beta-GAL) as well as the systematic conversion of the substrates (AP-RED/HRP-GREEN/beta-GAL-BLUE), which results in the development of strong, permanent red, green and blue signals that cannot be visualized by light microscopy, e.g., with a 40× dry lens.

While specific embodiments of the invention have been described in detail, it should be appreciated by those skilled in the art that various modifications and alternations and applications could be developed in light of the overall teachings of the disclosure. Accordingly, the particular arrangements, systems, apparatuses, and methods disclosed are meant to be illustrative only and not limiting as to the scope of the invention.

What is claimed is:

1. A method for detection of multiple different chromosome or DNA regions in a cell for detection of a structural chromosome aberration, wherein the chromosome aberration has at least a breaking point region 1 and a breaking point region 2 within a non-aberrant chromosome, based on directly or indirectly labeled nucleic acid fragments, wherein a first probe (probe A), labeled with a label A, and a second probe (probe B), labeled with a label B, flank the breaking point region 1 in the non-aberrant chromosome, forming fusion signals A-B, and two probes, a third probe and a fourth probe, each labeled with a label C (probes C), flank the breaking point region 2 in the non-aberrant chromosome, forming fusion signals C-C, wherein the breaking point region 1 and the breaking point region 2 are within the same chromosome, wherein the probes A, B and C have different labels and the fusion signals A-B and C-C change to fusion signals A-C and fusion signals B-C in the event of the chromosome aberration, and wherein the chromosome aberration is an inversion, insertion, and/or duplication of a short genomic section having a length of less than 20 Mb, wherein the method comprises:
contacting a sample with the probes; and
detecting the fusion signals.

2. The method according to claim 1, wherein the probes are polynucleotides, modified polynucleotides or modified nucleic acid fragments or oligonucleotides or modified oligonucleotides, and wherein the step of contacting the sample with the probes comprises hybridizing the sample and the probes.

3. The method according to claim 1, wherein the labels A, B, and C are selected from the group comprising dyes, dye substrates, chemiluminescent dyes, radioisotopes, spin labels, enzymes, haptens, quantum dots, beads, aminohexyls, pyrenes and fluorescent dyes, and the step of detecting the fusion signals comprises visualizing a signal from the labels.

4. The method according to claim 1, wherein the labels A, B, and C comprise three directly incorporated fluorescent dyes for the emission ranges green, red and blue, and the step of detecting the fusion signals comprises visualizing a fluorescent signal from the labels.

5. The method according to claim 1, wherein the labels A, B, and C comprise three directly incorporated fluorescent dyes for the emission ranges green, orange/red and gold, and the step of detecting the fusion signals comprises visualizing a fluorescent signal from the labels.

6. The method according to claim 1, wherein the labels A, B, and C comprise biotin, digoxigenin and DNP which bind to antibody-coupled alkaline phosphatase, antibody-coupled peroxidase and antibody-coupled beta-galactosidase, and the step of detecting the fusion signals comprises visualizing a bright field signal from the labels.

7. The method according to claim 1, wherein the inverted, inserted and/or duplicated genomic sections have a length of less than 15 Mb.

8. The method according to claim 1, wherein the altered fusion signals A-C or B-C are visible in the signal pattern as fusion signal A-C and signal C/signal B or as fusion signal B-C and signal C/signal A in a large breaking point region.

9. The method according to claim 1, wherein the method is for detection of differentiation inversions and translocations.

10. The method according to claim 1, wherein the method is for detection of inversions, wherein the inversion inv(2)(p22-p21p23) and/or the genes ALK and/or EML4 are affected.

11. A preparation for detection of multiple different chromosome regions or DNA regions in a cell for detection of a structural chromosome aberration, wherein the chromosome aberration has at least a breaking point region 1 and a breaking point region 2 within a non-aberrant chromosome, the preparation comprising:
  a first probe (probe A), labeled with a label A, and a second probe (probe B), labeled with a label B, wherein the first and second probe flank the breaking, point region 1 in the non-aberrant chromosome, forming fusion signals A-B, and
  two probes, a third probe and a fourth probe, each labeled with a label C (probes C), wherein the third and fourth probe flank the breaking point region 2 in the non-aberrant chromosome, forming fusion signals C-C,
  wherein the fusion signals A-B and C-C change to fusion signals A-C and fusion signals B-C in the event of the chromosome aberration, wherein the chromosome aberration is an inversion, insertion, and/or duplication of a short genomic section having a length of less than 20 Mb,
  wherein the probes are directly or indirectly labelled nucleic acid fragments,
  wherein the probes A, B and C have different labels, and
  wherein the breaking point region 1 and the breaking point region 2 are within the same chromosome.

12. The preparation according to claim 11, wherein the probes are polynucleotides, modified polynucleotides or modified nucleic acid fragments or oligonucleotides or modified oligonucleotides.

13. The preparation according to claim 11, wherein the labels A, B, and C on the probes are selected from the group comprising dyes, dye substrates, chemiluminescent dyes, radioisotopes, spin labels, enzymes, haptens, quantum dots, beads, aminohexyls, pyrenes and fluorescent dyes.

14. The preparation according to claim 11, wherein the labels A, B, and C on the probes are three directly incorporated fluorescent dyes for the emission ranges green, red and blue.

15. The preparation according to claim 11, wherein the labels A, B, and C on the probes are three directly incorporated fluorescent dyes for the emission ranges green, orange/red and gold.

16. The preparation according to claim 11, wherein the labels A, B, and C on the probes are biotin, digoxigenin and DNP which bind to antibody-coupled alkaline phosphatase, antibody-coupled peroxidase and antibody coupled beta-galactosidase.

* * * * *